(12) United States Patent
Mignani et al.

(10) Patent No.: US 9,242,956 B2
(45) Date of Patent: Jan. 26, 2016

(54) METHOD FOR PRODUCING POLYGLYCEROL (POLY)CARBONATE

(71) Applicants: RHODIA OPERATIONS, Paris (FR); UNIVERSITE CLAUDE BERNARD LYON 1, Villeurbanne (FR); CENTRE NATIONAL DE LA RECHERCHE SCIENTIFIQUE (C.N.R.S.), Paris (FR); FONDS DE DEVELOPPEMENT DES FILIERES DES OLEAGINEUX ET PROTEAGINEUX FIDOP, Paris (FR)

(72) Inventors: Gerard Mignani, Lyons (FR); Julien Debray, Glenac (FR); Eric Da Silva, Lyons (FR); Marc Lemaire, Villeurbanne (FR); Yann Raoul, Soissons (FR)

(73) Assignees: Rhodia Operations, Paris (FR); Universite Claude Bernard Lyon 1, Villeurbanne (FR); Centre National de la Recherche Scientifique-(CNRS), Paris (FR); Fonds De Developpement Des Filieres Des Oleagineux Et Proteagineux Fidop, Paris (FR)

( * ) Notice: Subject to any disclaimer, the term of this patent is extended or adjusted under 35 U.S.C. 154(b) by 0 days.

(21) Appl. No.: 14/413,527

(22) PCT Filed: Jul. 10, 2013

(86) PCT No.: PCT/EP2013/064595
§ 371 (c)(1),
(2) Date: Jan. 8, 2015

(87) PCT Pub. No.: WO2014/009421
PCT Pub. Date: Jan. 16, 2014

(65) Prior Publication Data
US 2015/0152079 A1    Jun. 4, 2015

(30) Foreign Application Priority Data
Jul. 11, 2012   (FR) .................................... 12 56678

(51) Int. Cl.
*C07D 317/08* (2006.01)
*C07D 317/36* (2006.01)

(52) U.S. Cl.
CPC .................................... *C07D 317/36* (2013.01)

(58) Field of Classification Search
CPC ............................. C07D 317/36; C07D 317/34
USPC ......................................................... 549/229
See application file for complete search history.

(56) References Cited

U.S. PATENT DOCUMENTS

| 6,025,504 A | 2/2000 | Claude et al. |
| 8,772,526 B2 * | 7/2014 | Jerome et al. ................. 558/236 |
| 2010/0209979 A1 | 8/2010 | Jung et al. |
| 2011/0201828 A1 | 8/2011 | Prochazka et al. |
| 2012/0264941 A1 | 10/2012 | Jerome et al. |

FOREIGN PATENT DOCUMENTS

| DE | 4129752 A1 | 3/1993 |
| EP | 0739888 A1 | 10/1996 |
| EP | 0955298 A1 | 11/1999 |
| JP | 06329663 A2 | 11/1994 |
| JP | H06329663 A | 11/1994 |
| WO | WO 98/24726 A1 | 6/1998 |
| WO | WO 2010043581 A1 | 4/2010 |
| WO | 2011/083255 A1 | 7/2011 |

OTHER PUBLICATIONS

Hatano, M. et al.—"Lanthanum (III) Isopropoxide Catalyzed Chemoselective Transesterification of Dimethyl Carbonate and Methyl Carbamates": Organic Letters, 2011, vol. 13, No. 3 pp. 430-433 (4 pages)—XP055018738.
Veldurthy, B. et al.—"An efficient synthesis of organic carbonates: atom economic protocol with a new catalytic system": Chem Communcation, 2004, pp. 734-735 (2 pages)—XP-002636595.
Translation of First Office Action issued Sep. 21, 2015 in corresponding Chinese application No. 201380037250.6 (12 pages).

* cited by examiner

*Primary Examiner* — T. Victor Oh
(74) *Attorney, Agent, or Firm* — Osha • Liang LLP

(57) ABSTRACT

The invention relates to a method for producing a compound of fonnula (I), comprising the reaction, in the presence of a catalytic system comprising a single rare earth oxide or a mixture of rare earth oxides, of an alkyl carbonate or an alkylene carbonate with a polyol of fonnula (II), wherein p is a whole number between 2 and 10.

17 Claims, No Drawings

METHOD FOR PRODUCING POLYGLYCEROL (POLY)CARBONATE

CROSS-REFERENCE TO RELATED APPLICATIONS

The present application is a U.S. national stage entry under 35 U.S.C. §371 of International Application No. PCT/EP2013/064595 filed Jul. 10, 2013, which claims priority to FR Application No. 12.56678 filed on Jul. 11, 2012, the whole content of this being herein incorporated by reference for all purposes.

The present invention relates to a method for producing polyglycerol (poly)carbonate.

Methods for the synthesis of glycerol carbonate are widely described in the literature.

Methods applying organic carbonates have been developed.

A method for preparing glycerol carbonate by reaction of glycerol and of a cyclic organic carbonate in the presence of a solid catalyst comprising a bicarbonated or hydroxylated anionic macroporous resin or a three dimensional zeolite of the X or Y type including basic sites at a temperature comprised between 50 and 110° C. is known notably from EP 0 739 888. The yield of the reaction is of the order of 90%. In order to obtain this yield, it is however necessary to draw off the ethylene glycol formed during the reaction. The method is applicable to pure glycerol as well as to glycerins.

A method for preparing glycerol carbonate by reaction between dimethyl carbonate and glycerol by transesterification catalysed by a lipase is also known from US2010/0209979.

JP06329663 discloses a method for preparing glycerol carbonate by reaction between ethylene carbonate and glycerol catalyzed by aluminium, magnesium, zinc, titanium, lead oxides. Other methods were developed by catalysis with CaO. However, these catalysts are not stable and are notably degraded by water and do not give the possibility of conducting the method continuously.

There exist other methods notably using phosgene and urea. The phosgene method, however, has the drawback of being highly toxic and is therefore not suitable for preparing products entering the manufacturing of food, cosmetic or pharmaceutical compositions.

From EP 0 955 298, a method for synthesis of glycerol carbonate is thus known, consisting in the reaction of glycerol with urea in the presence of a catalyst of the metal or organometal salt type and having Lewis acid sites. The obtained molar yield is comprised between 40 and 80% relatively to glycerol.

However, the methods with urea generate ammonia in a strong proportion, this ammonia therefore has to be neutralized as a salt and these ammonia salts are not recoverable. Drawbacks in terms of cost, difficulty of purification and sometimes observance of the environment (notably discharge of dioxane and/or glycidol, use of glycidol, use of a catalyst based on tin, use of acetonitrile) are also described.

There is therefore a need to provide a method which may easily be industrialized, which may be applied continuously and which does not have any risk notably in terms of toxicity.

The present invention relates to a method for preparing by transcarbonation a compound of formula (I)

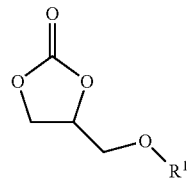

wherein $R^1$ represents:
  a $(CH_2CH(OH)CH_2O)_nH$ group; or
  a $(CH_2CH(OH)CH_2O)_mCH_2R^2$ group;
n representing an integer from 1 to 10, preferably from 1 to 5, for example n represents 1 or 2;
m representing an integer from 0 to 10, preferably from 0 to 5, for example m represents 0 or 1;
$R^2$ representing

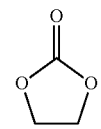

said method comprises the reaction, in the presence of a catalytic system comprising as a catalytic entity a rare earth oxide alone or a mixture of rare earth oxides, between an alkyl carbonate or an alkylene carbonate and a polyol of formula (II)

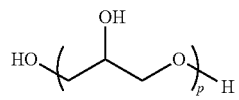

wherein p represents an integer from 2 to 10.

In an embodiment, in the compound of formula (I) $R^1$ represents $(CH_2CH(OH)CH_2O)_nH$.

In another embodiment, in the compound of formula (I) $R^1$ represents $(CH_2CH(OH)CH_2O)_mCH_2R^2$.

Preferably, in the compound of formula (II) p represents an integer from 2 to 5, preferably 2 or 3.

Within the scope of the present invention, the expression <<comprised between x and y>> means that it also covers the limits x and y. Thus, <<comprised between x and y>> may be understood, within the scope of the invention, as meaning <<ranging from x to y>>.

In the method according to the invention, the alkyl carbonate may be a compound of formula (III)

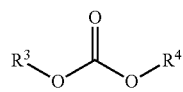

wherein $R^3$ and $R^4$, either identical or different, represent:
  a linear or branched $C_1$-$C_{20}$ alkyl group;
  a $C_5$-$C_{14}$, preferably $C_6$-$C_{14}$ aryl group; optionally substituted with one or several substituents, notably selected from:
    a $C_1$-$C_9$, preferably $C_1$-$C_5$ alkyl group;

a $C_5$-$C_{14}$, preferably $C_6$-$C_{14}$, preferably $C_6$-$C_{10}$ aryl group, optionally substituted;
an alkyl-aryl group of formula -$Q^1$-$Ar^1$ wherein $Q^1$ represents a $C_1$-$C_9$, preferably $C_1$-$C_5$ alkyl radical and $Ar^1$ represents a $C_6$-$C_{14}$, preferably $C_6$ aryl group, optionally substituted;
a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;
a $C_1$-$C_9$, preferably $C_1$-$C_5$ alkoxy group;
a $C_5$-$C_6$ cycloalkyl group optionally substituted with one or several substituents, notably selected from:
a $C_1$-$C_9$, preferably $C_1$-$C_5$ alkyl group;
a $C_5$-$C_{14}$, preferably $C_6$-$C_{14}$, preferably $C_6$-$C_{10}$ aryl group, optionally substituted;
an alkyl-aryl group of formula -$Q^2$-$Ar^2$ wherein $Q^2$ represents a $C_1$-$C_9$, preferably $C_1$-$C_5$ alkyl radical and $Ar^2$ represents a $C_6$-$C_{14}$, preferably $C_6$ aryl group, optionally substituted;
a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;
a $C_1$-$C_9$, preferably $C_1$-$C_5$ alkoxy group; or
a heteroaryl group, preferably comprising 5 to 10 members, preferably comprising 1 to 2 heteroatoms, notably selected from oxygen, nitrogen or sulfur; optionally substituted with one or several substituents notably selected from:
a $C_1$-$C_9$, preferably $C_1$-$C_5$ alkyl group;
a $C_5$-$C_{14}$, preferably $C_6$-$C_{14}$, preferably $C_6$-$C_{10}$ aryl group, optionally substituted;
an alkyl-aryl group of formula -$Q^3$-$Ar^3$ wherein $Q^3$ represents a $C_1$-$C_9$, preferably $C_1$-$C_5$ alkyl radical and $Ar^3$ represents a $C_6$-$C_{14}$, preferably $C_6$ aryl group, optionally substituted;
a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;
a $C_1$-$C_9$, preferably $C_1$-$C_5$ alkoxy group;
an alkyl-aryl group of formula -$Q^4$-$Ar^4$ wherein $Q^4$ represents a $C_1$-$C_9$, preferably $C_1$-$C_5$ alkyl radical and $Ar^4$ represents a $C_6$-$C_{14}$, preferably $C_6$ aryl group, optionally substituted.

Preferably in the method of the invention, $R^3$ and $R^4$, either identical or different, represent:
a linear or branched $C_1$-$C_{10}$ alkyl group, for example a methyl, ethyl, propyl, butyl;
a $C_6$, $C_{10}$ or $C_{14}$ aryl group, optionally substituted with one or several substituents, notably selected from:
a $C_1$-$C_5$ alkyl group, for example methyl, ethyl; a phenyl group, optionally substituted;
an alkyl-aryl group of formula -$Q^1$-$Ar^1$ wherein $Q^1$ represents a $C_1$-$C_9$ preferably $C_1$-$C_5$ alkyl radical and $Ar^1$ represents a phenyl group optionally substituted, preferably a methylphenyl, ethylphenyl;
a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;
a $C_1$-$C_5$ alkoxyl group, for example a methoxy, ethoxy;
a $C_5$-$C_6$ cycloalkyl group optionally substituted with one or several substituents, notably selected from:
a $C_1$-$C_5$ alkyl group, for example a methyl, ethyl; a phenyl group optionally substituted;
an alkyl-aryl group of formula -$Q^2$-$Ar^2$ wherein $Q^2$ represents a $C_1$-$C_9$, preferably $C_1$-$C_5$ alkyl radical and $Ar^2$ represents a phenyl group optionally substituted, preferably a methylphenyl, ethylphenyl;
a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;
a $C_1$-$C_5$ alkoxy group, for example a methoxy, ethoxy; or
a heteroaryl group preferably comprising 5 to 10 members, preferably comprising 1 to 2 heteroatoms, notably selected from oxygen, nitrogen or sulfur, for example aniline, optionally substituted with one or several substituents, notably selected from
a $C_1$-$C_5$ alkyl group, for example a methyl, ethyl; a phenyl group optionally substituted;
an alkyl-aryl group of formula -$Q^3$-$Ar^3$ wherein $Q^3$ represents a $C_1$-$C_9$, preferably $C_1$-$C_5$ alkyl radical and $Ar^3$ represents a phenyl group optionally substituted, preferably a methylphenyl, ethylphenyl;
a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;
a $C_1$-$C_5$ alkoxy group, for example a methoxy, ethoxy;
an alkyl-aryl group of formula -$Q^4$-$Ar^4$ wherein $Q^4$ represents a $C_1$-$C_9$, preferably $C_1$-$C_5$ alkyl radical and $Ar^4$ represents a phenyl group optionally substituted.

Advantageously, the alkyl carbonate is dimethyl carbonate, diethyl carbonate. Preferably, the alkyl carbonate is dimethyl carbonate.

According to the invention, by an alkylene carbonate is meant a compound of formula (IV)

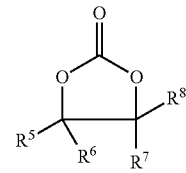

(IV)

wherein
$R^5$, $R^6$, $R^7$ and $R^8$ either identical or different are selected from:
a hydrogen;
a linear, branched or cyclic $C_1$-$C_9$, preferably $C_1$-$C_5$ hydrocarbon group which may comprise one or several heteroatoms, notably selected from oxygen, nitrogen or sulfur, and may comprise one or several substituents OH;
a group of formula —$CH_2$—$R^{10}$, wherein $R^{10}$ represents a linear, branched or cyclic $C_1$-$C_9$, preferably $C_1$-$C_5$ hydrocarbon group which may comprise one or several heteroatoms, notably selected from oxygen, nitrogen or sulfur, and may comprise one or several substituents OH;
a group of formula $C(O)OR^{11}$, wherein $R^{11}$ represents a hydrogen atom, a $C_1$-$C_9$, preferably $C_1$-$C_5$ alkyl group for example a methyl, ethyl;
a $C_5$-$C_6$ cycloalkyl group optionally substituted with one or several substituents notably selected from:
a $C_1$-$C_9$, preferably $C_1$-$C_5$ alkyl group; a $C_5$-$C_{14}$, preferably $C_6$-$C_{14}$, preferably $C_6$-$C_{10}$ aryl group, optionally substituted;

an alkyl-aryl group of formula -$Q^5$-$Ar^5$ wherein $Q^5$ represents a $C_1$-$C_9$, preferably $C_1$-$C_5$ alkyl radical and $Ar^5$ represents a $C_6$-$C_{14}$, preferably $C_6$ aryl group, optionally substituted;

a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;

a $C_1$-$C_9$, preferably $C_1$-$C_5$ alkoxy group;

a heteroaryl group, preferably comprising 5 to 10 members, preferably comprising 1 to 2 heteroatoms, notably selected from oxygen, nitrogen or sulfur optionally substituted with one or several substituents notably selected from:

a $C_1$-$C_9$, preferably $C_1$-$C_5$ alkyl group; a $C_5$-$C_{14}$, preferably $C_6$-$C_{14}$, preferably $C_6$-$C_{10}$ aryl group, optionally substituted;

an alkyl-aryl group of formula -$Q^6$-$Ar^6$ wherein $Q^6$ represents a $C_1$-$C_9$, preferably $C_1$-$C_5$ alkyl radical and $Ar^6$ represents a $C_6$-$C_{14}$, preferably $C_6$ aryl group, optionally substituted;

a polyalkoxy group of formula —$(OCH_2CH_2)_q$—$OR^9$ wherein n represents an integer comprised between 2 and 5 and $R^{15}$ represents a $C_1$-$C_{10}$, preferably $C_1$-$C_5$ alkyl group;

a $C_1$-$C_9$, preferably $C_1$-$C_5$ alkoxy group;

a $C_6$-$C_{14}$ aryl group, optionally substituted with one or several substituents, notably selected from:

a $C_1$-$C_9$, preferably $C_1$-$C_5$ alkyl group; a $C_5$-$C_{14}$, preferably $C_6$-$C_{14}$, preferably $C_6$-$C_{10}$ alkyl group, optionally substituted;

an alkyl-aryl group of formula -$Q^7$-$Ar^7$ wherein $Q^7$ represents a $C_1$-$C_9$, preferably $C_1$-$C_5$ alkyl radical and $Ar^7$ represents a $C_6$-$C_{14}$, preferably $C_6$ aryl group, optionally substituted;

a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;

a $C_1$-$C_9$, preferably $C_1$-$C_5$ alkoxy group;

an alkyl-aryl group of formula -$Q^8$-$Ar^8$ wherein $Q^8$ represents a $C_1$-$C_9$, preferably $C_1$-$C_5$ alkyl radical and $Ar^8$ represents a $C_6$-$C_{14}$, preferably $C_6$ aryl group, optionally substituted;

or one of the $R^5$/$R^6$ and one of the $R^7$/$R^8$ form together with the carbon atoms which bear them a double bond; or one of the $R^5$/$R^6$ and one of the $R^7$/$R^8$ form together with the carbon atoms bearing them a double bond which is comprised in an aryl, notably phenyl group, formed by $R^6$ and $R^7$ with the two carbon atoms bearing them.

Preferably in the method of the invention $R^5$, $R^6$, $R^7$ and $R^8$, either identical or different are selected from:

a hydrogen;

a linear or branched $C_1$-$C_9$, preferably $C_1$-$C_5$ alkyl group which may comprise one or several heteroatoms, notably selected from oxygen, nitrogen or sulfur, and may comprise one or several substituents OH; for example methylene, ethylene;

a group of formula —$CH_2$—$R^{10}$, wherein $R^{10}$ represents a linear or branched $C_1$-$C_5$ hydrocarbon group which may comprise one or several heteroatoms, notably selected from oxygen, nitrogen or sulfur and may comprise one or several substituents OH, for example ethylene, methylene;

a group of formula $C(O)OR^{11}$, wherein $R^{11}$ represents a hydrogen atom, a $C_1$-$C_5$ alkyl group, for example a methyl, ethyl;

a $C_5$-$C_6$ cycloalkyl group optionally substituted with one or several substituents notably selected from:

a $C_1$-$C_5$ alkyl group, for example methyl, ethyl; a phenyl group optionally substituted;

an alkyl-aryl group of formula -$Q^5$-$Ar^5$ wherein $Q^5$ represents a $C_1$-$C_9$, preferably $C_1$-$C_5$ alkyl radical and $Ar^5$ represents a phenyl group optionally substituted, preferably methylphenyl, ethylphenyl;

a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;

a $C_1$-$C_5$ alkoxy group, for example a methoxy, ethoxy;

a heteroaryl group, preferably comprising 5 to 10 members, preferably comprising 1 to 2 heteroatoms, notably selected from oxygen, nitrogen or sulfur, for example aniline, optionally substituted with one or several substituents, notably selected from:

a $C_1$-$C_5$ alkyl group, for example a methyl, ethyl; a phenyl group optionally substituted;

an alkyl-aryl group of formula -$Q^6$-$Ar^6$ wherein $Q^6$ represents a $C_1$-$C_9$, preferably $C_1$-$C_5$ alkyl radical and $Ar^6$ represents a phenyl group optionally substituted, preferably a methylphenyl, ethylphenyl;

a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;

a $C_1$-$C_5$ alkoxy group, for example a methoxy, ethoxy;

a $C_6$, $C_{10}$ or $C_{14}$ aryl group, optionally substituted with one or several substituents notably selected from:

a $C_1$-$C_5$ alkyl group, for example a methyl, ethyl;

a phenyl group optionally substituted; an alkyl-aryl group of formula -$Q^7$-$Ar^7$ wherein $Q^7$ represents a $C_1$-$C_9$, preferably $C_1$-$C_5$ alkyl radical and $Ar^7$ represents a phenyl group optionally substituted, preferably a methylphenyl, ethylphenyl;

a polyalkoxy group of formula —$(OCH_2CH_2)_q$—$OR^9$ wherein q represents an integer comprised between 2 and 5 and $R^9$ represents a $C_1$-$C_{10}$, preferably $C_1$-$C_5$ alkyl group;

a $C_1$-$C_5$ alkoxy group, for example a methoxy, ethoxy;

an alkyl-aryl group of formula -$Q^8$-$Ar^8$ wherein $Q^8$ represents a $C_1$-$C_9$, preferably $C_1$-$C_5$ alkyl radical and $Ar^8$ represents an optionally substituted phenyl;

or one of the $R^5$/$R^6$ and one of the $R^7$/$R^8$ form together with the carbon atoms bearing them a double bond; or one of the $R^5$/$R^6$ and one of the $R^7$/$R^8$ form together with the carbon atoms bearing them a double bond which is comprised in an aryl group, notably phenyl, formed by $R^6$ and $R^7$ with the two carbon atoms bearing them.

Advantageously, the alkyl carbonate may be ethylene carbonate, propylene carbonate, dibutylene carbonate or dihexylene carbonate.

According to the invention, the catalytic system comprises as a catalytic entity, a rare earth oxide or a mixture of rare earth oxides.

In an embodiment of the invention, the catalytic system consists of a catalytic entity selected from rare earth oxides or mixtures thereof.

By rare earth (Ln), are meant chemical elements selected from the group formed by scandium, yttrium and chemical elements with an atomic number from 57 to 71. Advantageously, the rare earths are selected from cerium (Ce), lanthanum (La), praseodymium (Pr), neodymium (Nd), yttrium (Y), gadolinium (Gd), samarium (Sm) and holmium (Ho), alone or as a mixture, preferably cerium, lanthanum, praseodymium, samarium, yttrium and neodymium, or mixtures thereof.

According to the invention, the rare earth oxides are selected from $CeO_2$; $Pr_6O_{11}$, rare earth oxides of formula $Ln_2O_3$ wherein Ln represents lanthanum, neodymium, yttrium, gadolinium, samarium or holmium; alone or as a mixture.

Advantageously, the rare earth oxides are selected from $La_2O_3$, $CeO_2$, $Pr_6O_{11}$, $Nd_2O_3$, $Sm_2O_3$, $Y_2O_3$, alone or as a mixture, preferably $La_2O_3$. As a particular mixture, mention may for example be made of $CeO_2/Pr_6O_{11}$.

Preferably, the rare earth oxide is $La_2O_3$.

Preferably, the rare earth oxide is CeO.

Generally, the catalytic system according to the invention consists of a catalytic entity in solid form, thereby allowing its use in a continuous method. The catalyst may notably be found in monolithic form (forming a single inert, rigid, porous block) or in an extruded form.

The catalytic system may also comprise an inert support on which is deposited the catalytic entity. The catalytic system comprising a support according to the invention may be in an extruded form, in the form of a coating having catalytic properties and based on a rare earth oxide or on a mixture of rare earth oxides and optionally of a binder of a known type on a substrate of the monolithic metal or ceramic type. Advantageously, it is in an extruded form. The extruded form advantageously gives the possibility of shaping the method of the invention continuously, which is not possible with a powder catalyst which would obstruct the different elements of the reactor.

For the method according to the invention, by extruded catalytic system is meant any catalytic system obtained by ejection under pressure of a slurry through nozzles or dies of selected shapes. The thereby obtained catalytic systems may have various forms, they may for example have cylindrical or half-cylindrical, square, polygonal sections or further sections in the form of lobes, such as tri-lobes. The catalytic systems may be solid or hollow, they may have the form of a monolith or of a honeycomb. These extruded catalytic systems may notably be obtained by the method as described on pages 4 to 10 of the patent application WO98/24726.

By inert support is meant a support which does not come into play, as a catalyst or as a reagent, in the transcarbonation reaction of the invention and this regardless of the pH. Typically, the support is neutral, i.e. it does not substantially modify the catalytic activity of the catalytic entity. The support may also be described as inactive in so far that it does not have any catalytic activity for the reaction and does not modify the catalytic activity of the catalytic entity. The supports are selected from extrudable and non-hydrolyzable supports or monolithic and non-hydrolyzable supports.

Preferably, the support may be selected from extrudable and non-hydrolyzable metal oxides, clays, active coals (black coals), ceramic or metal monoliths.

The support may for example be selected from titanium oxides, zirconium oxides, iron oxides; aluminium oxides, notably alundum; silica-alumina, for example clays; active coals; Kieselguhr.

This may also be corundum, silica carbide, pumice.

Among extrudable and non-hydrolyzable metal oxides, mention may preferably be made of titanium oxides, zirconium oxides, iron oxides, aluminium oxides, preferably titanium oxides, zirconium oxides, neutral alumina. More preferably, the support is selected from titanium oxides, zirconium oxides, iron oxides, aluminium oxides, notably neutral alumina, active coals preferably titanium oxides, zirconium oxides, neutral aluminas, active coals.

The amount of catalytic entity on the support may be comprised between 0.05 to 25% by mole based on the number of moles of the support, preferably from 1 to 10% molar. It should be noted that this value notably depends on the nature of the support, on its specific surface area, on its porosity and on the desired catalytic properties.

According to the invention, the catalytic system may notably have a specific surface area of at least $1\,m^2/g$, preferably the specific surface area is comprised between 1 and 150 $m^2/g$, more preferentially comprised between 3 and $100\,m^2/g$. One skilled in the art is able to adjust this specific surface area for example by calcination of the catalytic system.

According to the invention, the catalytic system may be doped with metals of the Lewis acid type, for example transition metals, earth-alkaline metals and metalloids. Advantageously, these catalytic entities form with the dopants solid solutions forming an entity unit.

These metals may be selected from iron ($Fe^{II}$ and $Fe^{III}$), copper ($Cu^{I}$ and $Cu^{II}$), aluminium ($Al^{III}$), titanium ($Ti^{IV}$), boron ($B^{III}$), zinc ($Zn^{II}$) and magnesium ($Mg^{II}$). Preferably these metals are selected from the group formed by iron ($Fe^{II}$ and $Fe^{III}$), copper ($Cu^{I}$ and $Cu^{II}$), titanium ($Ti^{IV}$) and zinc ($Zn^{II}$).

In the method of the invention, the relative percentage of metal relatively to the catalytic entity may be comprised between 0.01 and 10% by moles, preferably between 1 and 10% by moles, for example between 1 and 5% by moles.

Advantageously, the catalytic systems of the invention are stable towards water. For example the catalysts of the invention may contain less than 5% by weight of water. This advantageously gives the possibility of conducting the transcarbonation reaction in a medium containing water, for example in a medium containing less than 15% by weight of water, for example less than 5% by weight of water. Thus, and unlike the method of the state of the art, it is not necessary to have significant control of the amount of water in the reaction medium and it is not necessary to apply reagents free of water. This notably has advantages in terms of costs.

The catalyst according to the invention may advantageously be easily recovered after reaction with any method known to one skilled in the art, notably by decantation or filtration.

The method according to the invention is conducted at atmospheric pressure or autogenous pressure.

By autogenous pressure is meant the pressure inside the reactor which is due to the reagents used. In the case of the present invention, by autogenous pressure is meant a pressure of less than 1 MPa, preferably less than 0.5 MPa, preferably less than 0.3 MPa, for example less than 0.2 MPa.

According to the invention, the method according to the invention is applied at a temperature comprised between 25 and 250° C., preferably between 25 and 200° C., for example between 50 and 125° C.

Advantageously, the polyol/alkyl carbonate or polyol/alkylene carbonate molar ratio is comprised between 1/30 and 1/1, preferably between 1/20 and 1/1, for example between 1/15 and 1/1.

Advantageously, the polyol/alkyl carbonate or polyol/alkylene carbonate molar ratio is comprised between 1/30 and 1/10, preferably between 1/30 and 1/15 and the compound of formula (I) is a compound in which $R^1$ represents $(CH_2CH(OH)CH_2O)_m CH_2R^2$.

Advantageously, the polyol/alkyl carbonate or polyol/alkylene carbonate molar ratio is comprised between 1/8 and 1/1, preferably between 1/5 and 1/1 and the compound of formula (I) is a compound in which $R^1$ represents $(CH_2CH(OH)CH_2O)_nH$.

Advantageously, the amount of catalytic entity is comprised between 0.01 and 50% molar based on the number of moles of polyol, preferably between 1 and 25% molar, preferably between 3 and 15% molar.

The method according to the invention gives the possibility of obtaining the compound of formula (I) with good yields.

Advantageously, the method according to the invention is applied in the absence of a solvent. The polyol may be used as a solvent in the reaction according to the invention.

The method according to the invention may be applied continuously or batch wise. Advantageously, the method according to the invention is applied continuously.

According to the invention, the method may comprise a preliminary step for preparing an alkyl carbonate or an alkylene carbonate. This preliminary step is achieved by reaction between an alcohol or a mixture of alcohols or a diol and $CO_2$, in the presence of a catalytic system consisting of a catalytic entity selected from rare earth oxides and mixtures of rare earth oxides and optionally of a support.

The catalytic entity and the support are as defined for the transcarbonation method according to the invention.

Advantageously, the molar ratio between alcohol or diol and $CO_2$ is comprised between 1 and 150 equivalents in moles, preferably between 1 and 100 equivalents.

According to the invention, the preliminary step for preparing an alkyl carbonate or an alkylene carbonate is applied at an autogenous pressure or at atmospheric pressure.

According to the invention, the preliminary step for preparing an alkyl carbonate or an alkylene carbonate is applied at a temperature comprised between 25 and 250° C., preferably between 25 and 200° C., for example between 50 and 150° C.

Advantageously, the amount of catalytic system is comprised between 0.01 and 50% by mass based on the weight of alcohol, of a mixture of alcohols or of diol, preferably between 1 and 25% by mass, preferably between 3 and 15% by mass.

According to the invention, the alcohol fits the formula $R^{12}OH$ wherein $R^{12}$ represents:
- a linear or branched $C_1$-$C_{20}$ alkyl group;
- a $C_5$-$C_{14}$ aryl group optionally substituted with one or several substituents, notably selected from:
  - a $C_1$-$C_9$, preferably $C_1$-$C_5$ alkyl group;
  - a $C_5$-$C_{14}$, preferably $C_6$-$C_{14}$, preferably $C_6$-$C_{10}$ aryl group, optionally substituted;
  - an alkyl-aryl group of formula $-Q^1$-$Ar^1$ wherein $Q^1$ represents a $C_1$-$C_9$, preferably $C_1$-$C_5$ alkyl radical and $Ar^9$ represents a $C_6$-$C_{14}$, preferably $C_6$ aryl group, optionally substituted;
  - a polyalkoxy group of formula $-(OCH_2CH_2)_q-OR^9$ wherein n represents an integer comprised between 2 and 5 and $R^9$ represents a $C_1$-$C_{10}$, preferably $C_1$-$C_5$ alkyl group;
  - a $C_1$-$C_9$, preferably $C_1$-$C_5$ alkoxy group;
- a $C_5$-$C_6$ cycloalkyl group optionally substituted with one or several substituents notably selected from:
  - a $C_1$-$C_9$, preferably $C_1$-$C_5$ alkyl group;
  - a $C_5$-$C_{14}$, preferably $C_6$-$C_{14}$, preferably $C_6$-$C_{10}$ aryl group, optionally substituted;
  - an alkyl-aryl group of formula $-Q^2$-$Ar^2$ wherein $Q^2$ represents a $C_1$-$C_9$, preferably $C_1$-$C_5$ alkyl radical and $Ar^2$ represents a $C_6$-$C_{14}$, preferably $C_6$ aryl group, optionally substituted;
  - a polyalkoxy group of formula $-(OCH_2CH_2)_q-OR^9$ wherein q represents an integer comprised between 2 and 5 and $R^9$ represents a $C_1$-$C_{10}$, preferably $C_1$-$C_5$ alkyl group;
  - a $C_1$-$C_9$, preferably $C_1$-$C_5$ alkoxy group; or
- a heteroaryl group, preferably comprising 5 to 10 members, preferably comprising 1 to 2 heteroatoms, notably selected from oxygen, nitrogen or sulfur; optionally substituted with one or several substituents, notably selected from:
  - a $C_1$-$C_9$, preferably $C_1$-$C_5$ alkyl group;
  - a $C_5$-$C_{14}$, preferably $C_6$-$C_{14}$, preferably $C_6$-$C_{10}$ aryl group, optionally substituted;
  - an alkyl-aryl group of formula $-Q^3$-$Ar^3$ wherein $Q^3$ represents a $C_1$-$C_9$, preferably $C_1$-$C_5$ alkyl radical and $Ar^3$ represents a $C_6$-$C_{14}$, preferably $C_6$ aryl group, optionally substituted;
  - a polyalkoxy group of formula $-(OCH_2CH_2)_q-OR^9$ wherein q represents an integer comprised between 2 and 5 and $R^9$ represents a $C_1$-$C_{10}$, preferably $C_1$-$C_5$ alkyl group;
  - a $C_1$-$C_9$, preferably $C_1$-$C_5$ alkoxy group;
- an alkyl-aryl group of formula $-Q^4$-$Ar^4$ wherein $Q^4$ represents a $C_1$-$C_9$, preferably $C_1$-$C_5$ alkyl radical and $Ar^4$ represents a $C_6$-$C_{14}$, preferably $C_6$ aryl group, optionally substituted.

Preferably in the method of the invention, $R^{12}$ represents:
- a linear or branched $C_1$-$C_{10}$ alkyl group, for example a methyl, ethyl, propyl, butyl;
- a $C_6$, $C_{10}$ or $C_{14}$ aryl group, optionally substituted with one or several substituents, notably selected from:
  - a $C_1$-$C_5$ alkyl group, for example methyl, ethyl; a phenyl group, optionally substituted;
  - an alkyl-aryl group of formula $-Q^1$-$Ar^1$ wherein $Q^1$ represents a $C_1$-$C_9$ preferably $C_1$-$C_5$ alkyl radical and $Ar^1$ represents a phenyl group optionally substituted, preferably a methylphenyl, ethylphenyl;
  - a polyalkoxy group of formula $-(OCH_2CH_2)_q-OR^9$ wherein q represents an integer comprised between 2 and 5 and $R^9$ represents a $C_1$-$C_{10}$, preferably $C_1$-$C_5$ alkyl group;
  - a $C_1$-$C_5$ alkoxy group, for example a methoxy, ethoxy;
- a $C_5$-$C_6$ cycloalkyl group optionally substituted with one or several substituents, notably selected from:
  - a $C_1$-$C_5$ alkyl group, for example a methyl, ethyl; a phenyl group optionally substituted;
  - an alkyl-aryl group of formula $-Q^2$-$Ar^2$ wherein $Q^2$ represents a $C_1$-$C_9$, preferably $C_1$-$C_5$ alkyl radical and $Ar^2$ represents a phenyl group optionally substituted, preferably a methylphenyl, ethylphenyl;
  - a polyalkoxy group of formula $-(OCH_2CH_2)_q-OR^9$ wherein q represents an integer comprised between 2 and 5 and $R^9$ represents a $C_1$-$C_{10}$, preferably $C_1$-$C_5$ alkyl group;
  - a $C_1$-$C_5$ alkoxy group, for example a methoxy, ethoxy; or
- a heteroaryl group preferably comprising 5 to 10 members, preferably comprising 1 to 2 heteroatoms, notably selected from oxygen, nitrogen or sulfur, for example aniline, optionally substituted with one or several substituents, notably selected from:
  - a $C_1$-$C_5$ alkyl group, for example a methyl, ethyl; a phenyl group optionally substituted;
  - an alkyl-aryl group of formula $-Q^3$-$Ar^3$ wherein $Q^3$ represents a $C_1$-$C_9$, preferably $C_1$-$C_5$ alkyl radical and $Ar^3$ represents a phenyl group optionally substituted, preferably a methylphenyl, ethylphenyl;

a polyalkoxy group of formula —(OCH$_2$CH$_2$)$_q$—OR$^9$ wherein q represents an integer comprised between 2 and 5 and R$^9$ represents a C$_1$-C$_{10}$, preferably C$_1$-C$_5$ alkyl group;

a C$_1$-C$_5$ alkoxy group, for example a methoxy, ethoxy;

an alkyl-aryl group of formula -Q$^4$-Ar$^4$ wherein Q$^4$ represents a C$_1$-C$_9$, preferably C$_1$-C$_5$ alkyl radical and Ar$^4$ represents a phenyl group optionally substituted.

According to the invention, the diol fits the formula (V)

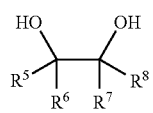

wherein

R$^5$, R$^6$, R$^7$ and R$^8$ either identical or different are as defined earlier.

By a continuous method is meant a method in which the reagents are brought continuously into the reactor and the products are drawn off from the reaction medium, continuously and then separated. The unreacted reagents may be reintroduced into the reaction medium or else removed.

The invention will now be described by means of examples, the latter being given as an illustration without however being limiting.

EXAMPLE 1

Synthesis of Diglycerol Monocarbonate

In a 50 ml flask, provided with a condenser, 7 g (42 mmol) of diglycerol (purity ≥80%) and 15.2 g (168 mmol) of dimethyl carbonate are introduced. The mixture is then brought to 90° C. and 0.7 g (2.1 mmol, 5 mol %) of lanthanide oxide are added. The reaction medium is heated to 120° C. for 24 hours. The solution is then filtered. After evaporation of dimethyl carbonate, the obtained product is purified by a chromatographic column on a flash silica column (Eluent (dichloromethane/MeOH: 9/1)) in order to obtain diglycerol mono carbonate with an isolated yield of 81% and diglycerol dicarbonate with an isolated yield of 19%.

EXAMPLE 2

Synthesis of Triglycerol Monocarbonate

In a 50 ml flask, provided with a condenser, 7 g (29 mmol) of triglycerol and 10.5 g (116 mmol) of dimethyl carbonate are introduced. The mixture is then brought to 90° C. and 0.47 g (1.5 mmol, 5 mol %) of lanthanide oxide are added. The reaction medium is heated to 120° C. for 24 hours. The solution is then filtered. After evaporation of dimethyl carbonate, the obtained product is purified by a chromatographic column on a flash silica column (eluent (dichloromethane/MeOH: 9/1)) in order to obtain triglycerol monocarbonate with an isolated yield of 80% and triglycerol dicarbonate with an isolated yield of 20%.

EXAMPLE 3

Synthesis of Diglycerol Dicarbonate

In a 100 ml flask, provided with a condenser, 5 g (30 mmol) of diglycerol (purity 80%) and 40.7 g (450 mmoles) of dimethyl carbonate are introduced. The mixture is then brought to 90° C. and 0.5 g (1.5 mmol, 5 mol %) of lanthanide oxide are added. The reaction medium is heated to 120° C. for 48 hours. The solution is then filtered. After evaporation of dimethyl carbonate, the product is crystallized from methanol in order to obtain after filtration of the solution, diglycerol dicarbonate with an isolated yield of 90%.

The following table groups the results of the different applied tests.

| Inlet | Catalyst | Obtained products | Conversion in % | Isolated yield in % |
|---|---|---|---|---|
| 1 | | (structure) | | 81 |
| | La$_2$O$_3$ | — | >99 | — |
| | | (structure) | | 19 |
| 2 | | (structure) | | 80 |
| | La$_2$O$_3$ | — | >99 | — |
| | | (structure) | | 20 |

-continued

| Inlet | Catalyst | Obtained products | Conversion in % | Isolated yield in % |
|---|---|---|---|---|
| 3 | $La_2O_3$ | 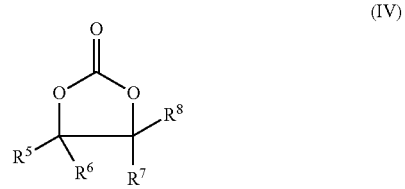 | >99 | 90 |

The method according to the invention therefore gives the possibility of obtaining in a simple and efficient way polyglycerol (poly)carbonates.

The invention claimed is:

1. A method for preparing by transcarbonation of a compound of formula (I),

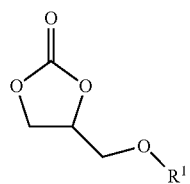

(I)

wherein $R^1$ represents:
a $(CH_2CH(OH)CH_2O)_n$H group; or
a $(CH_2CH(OH)CH_2O)_m CH_2R^2$ group;
n representing an integer from 1 to 10;
m representing an integer from 0 to 10;
$R^2$ representing

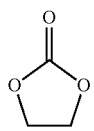

said method comprising the reaction, in the presence of a catalytic system comprising as a catalytic entity selected from a group consisting of a rare earth oxide alone and a mixture of rare earth oxides, between an alkyl carbonate or an alkylene carbonate and a polyol of formula (II)

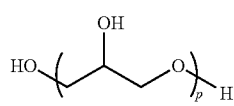

(II)

wherein p represents an integer from 2 to 10.

2. The method according to claim 1 wherein the alkyl carbonate is a compound of formula (III):

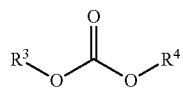

(III)

wherein $R^3$ and $R^4$, either identical or different, represent:

a linear or branched $C_1$-$C_{20}$ alkyl group;
a $C_5$-$C_{14}$ aryl group;
a $C_5$-$C_6$ cycloalkyl group; or
a heteroaryl group;
an alkyl-aryl group of formula -$Q^4$-$Ar^4$ wherein $Q^4$ represents a $C_1$-$C_9$ alkyl radical and $Ar^4$ represents a $C_6$-$C_{14}$ aryl group.

3. The method according to claim 1 wherein the alkylene carbonate is a compound of formula (IV)

(IV)

wherein
$R^5$, $R^6$, $R^7$ and $R^8$ either identical or different are selected from:
a hydrogen;
a linear, branched or cyclic $C_1$-$C_9$ hydrocarbon group which may have one or several heteroatoms, and may have one or several substituents OH;
a group of formula —$CH_2$—$R^{10}$, wherein $R^{10}$ represents a linear, branched or cyclic $C_1$-$C_9$ hydrocarbon group which may have one or several heteroatoms, and may have one or several substituents OH;
a group of formula $C(O)OR^{11}$, wherein $R^{11}$ represents a hydrogen atom, a $C_1$-$C_9$ alkyl group;
a $C_5$-$C_6$ cycloalkyl group;
a heteroaryl group;
a $C_6$-$C_{14}$ aryl group;
an alkyl-aryl group of formula -$Q^8$-$Ar^8$ wherein $Q^8$ represents a $C_1$-$C_9$ alkyl radical, and $Ar^8$ represents a $C_6$-$C_{14}$ aryl group;
or one of the $R^5$/$R^6$ and one of the $R^7$/$R^8$ form together with the carbon atoms bearing them a double bond; or one of the $R^5$/$R^6$ and one of the $R^7$/$R^8$ form together with the carbon atoms bearing them a double bond which is comprised in an aryl group formed by $R^6$ and $R^7$ with the two carbon atoms bearing them.

4. The method according claim 1 wherein $R^1$ represents $(CH_2CH(OH)CH_2O)_n$H.

5. The method according to claim 1 wherein R' represents $(CH_2CH(OH)CH_2O)_m CH_2R^2$.

6. The method according to claim 1 wherein the rare earth oxides fit the formula $Ln_2O_3$, with Ln representing lanthanum, neodymium, yttrium, gadolinium, samarium or holmium; $CeO_2$ or $Pr_6O_{11}$, alone or as a mixture.

7. The method according to claim 6, wherein the rare earth oxides are selected from $La_2O_3$, $CeO_2$, $Pr_6O_{11}$, $Nd_2O_3$, $Sm_2O_3$, $Y_2O_3$, alone or as a mixture.

8. The method according to claim 1 wherein the catalytic system comprises an inert support selected from the group consisting of extrudable and non-hydrolyzable metal oxides, clays, active coals (black coals), ceramic monoliths, and metal monoliths.

9. The method according to claim 1 wherein the catalytic system is extruded.

10. The method according to claim 1 wherein the polyol/alkyl carbonate or polyol/alkylene carbonate molar ratio is comprised between 1/30 and 1/10.

11. The method according to claim 1 wherein the polyol/alkyl carbonate or polyol/alkylene carbonate molar ratio is comprised between 1/8 and 1/1.

12. The method according to claim 1, wherein the amount of catalytic entity is comprised between 0.01 and 50% molar based on the number of moles of polyol.

13. The method according to claim 1, applied continuously.

14. The method according to claim 1, wherein the polyol/alkyl carbonate or polyol/alkylene carbonate molar ratio is comprised between 1/30 and 1/15.

15. The method according to claim 1, wherein the polyol/alkyl carbonate or polyol/alkylene carbonate molar ratio is comprised between 1/5 and 1/1.

16. The method according to claim 1, wherein the amount of catalytic entity is comprised between 1 and 25% molar based on the number of moles of polyol.

17. The method according to claim 1, wherein the amount of catalytic entity is comprised between 3 and 15% molar based on the number of moles of polyol.

* * * * *